US00PP11304P

United States Patent [19]

Pouw

[11] Patent Number: Plant 11,304

[45] Date of Patent: Mar. 21, 2000

[54] HYBRID TEA ROSE PLANT NAMED 'RUITICA'

[75] Inventor: A. A. Pouw, Pl De Kwakel, Netherlands

[73] Assignee: De Ruiter's Nieuwe Rozen B.V., Pl De Kwakel, Netherlands

[21] Appl. No.: 09/028,613

[22] Filed: Feb. 24, 1998

[51] Int. Cl.[7] ..... A01H 5/00

[52] U.S. Cl. ..... Plt./134

[58] Field of Search ..... Plt./130, 133, 134

*Primary Examiner*—Howard J. Locker

*Attorney, Agent, or Firm*—Christie, Parker & Hale, LLP

[57] ABSTRACT

A new variety of hybrid tea rose plant producing pale yellow flowers.

2 Drawing Sheets

BACKGROUND OF THE INVENTION

The present invention relates to a new and distinct variety of rose plant of the hybrid tea rose class which was created by crossing undistributed, unnamed and unpatented seedlings as seed and pollen parents in The Netherlands. The varietal denomination of the new variety is 'Ruitica'.

SUMMARY OF THE INVENTION

Among the novel characteristics possessed by this new variety which distinguish it from its parents and all other varieties of which I am aware are its attractive cream colored flowers with long stems borne on a floriferous plant.

Asexual reproduction by budding of the new variety as performed in The Netherlands, shows that the foregoing and other distinguishing characteristics come true to form and are established and transmitted through succeeding propagations. The new variety has been reproduced through propagation by cuttings, grafting, budding and micropropagation.

BRIEF DESCRIPTION OF ILLUSTRATIONS

The accompanying two photographic illustrations show the new variety of hybrid tea rose plant in color as true as it is reasonably possible to attain in color illustrations of this character.

The first illustration is a close up view of the bloom, peduncle, and foliage.

The second illustration shows a new shoot, 1; compound 3-leaflet leaf, 2; compound 5-leaflet leaf (partially cut-off), 3; compound 7-leaflet leaf, 4; a steam, 5; buds, 6 and 7; a flower about ⅓ to ½ open, 8; a flower fully open, 9; and flowering stems 10, 11, and 12, with reproductive organs displayed.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary depending upon growing conditions under different climate, soil, and cultivation conditions.

Parentage: Seed and pollen parents are unnamed seedlings.
Class: Hybrid Tea.

The following further horticultural description is based on observations made of specimens grown under glass in Quito, Ecuador.

FLOWER

Blooming habit: Nearly continuous.

A. Bud:

(1) *Size.*—Medium, about 3 to 5 cm. long by about 3 to 4 cm. wide, before sepals fall. About 4 to 6 cm. long by about 3 to 4 to 5 cm. wide, after sepals separate further.

(2) *Form.*—Ovate (shape of longitudinal section just before separation of sepals); urn-shaped after sepals part and petals begin to separate (3) *Color.*—Before sepals separate, near 11C to 11D with pink to red coloring near 51B, on petal reverse seen on outer petals and red edge at petal top (4) *Sepals.*—Some longer than bud, several considerably foliaceious; near 139A on top surface of foliaceous sepals.

(5) *Peduncle.*—Long; strength-erect, strong, near 139B.

Flower: Medium; viewed from above — round; viewed from side — (a) upper part of fully opened flower, flat; (b) lower part of fully opened flower, concave.

(1) *Size.*—Average size when fully expanded about 11 to 13 cm. at about full open.

(2) *Borne.*—Singly, one to a stem.

(3) *Form.*—Pointed center, spiral imbricated, some outer petals reflex to points, some inner petals reflex to points and some roll under; some petals ruffled, many petaloids, flat top.

(4) *Petalage.*—Fully double, about 40.

(5) *Color.*—After sepals part and petals unfurl color of petal top surface appears near 11C to 11D with slight pink washing, near 52C to 52D, on very outer petals; center of flower where petals bunch is slightly deeper toned yellow; Petal undersurface exhibits near 62D washing and veining against near 11C to 11D. Color at point of petal attachment is near 3D. Overall tonality from a distance is pale yellow to cream flowers.

(6) *Peduncle.*—Generally smooth.

(7) *Fragrance.*—Weak.

*Length of stems.*—About 60 cm. to 100 cm.

Petals:

(1) *Texture.*—Crisp.

(2) *Appearance.*—Inside velvety and outside satiny.

(3) *Form and size.*—Broad, medium, weak undulation of margin.

(4) *Arrangement.*—Regularly arranged, imbricated.
(5) *Petaloids.*—About 35.
(6) *Lasting quality.*—Long-lasting quality on plant (about 3 to 4 weeks) and after cutting (about 2 weeks).

REPRODUCTIVE ORGANS

A. Stamens, filaments and anthers:
*Arrangement and color.*—Regularly arranged around styles; color of filaments — yellow.
B. Pollen:
*Color.*—Near 11B.
C. Styles: Long, stigma above mouth of receptacle, white.
D. Stigmas: Yellow.
E. Hip: Pitcher-shaped; medium seed vessel at petal fall.

PLANT

A. Form: Narrow, bushy, average disease resistance; height about 1.5 m, spread about 0.6 m.
B. Growth: Vigorous.
C. Foliage: Compound 3, 5 and 7 leaflets.
(1) *Size.*—3-lealet leaf, terminal leaflet about 8 to 9 cm. long; 5-leaflet leaf, terminal leaflet about 5 to 10 cm long; 7 leaflet leaf, terminal leaflet about 9 to 10 cm. long.
(2) *Quantity.*—Abundant.
(3) *Color.*—Juvenile foliage — top near 187A and near 185A to 185B underside; absent or weak anthocyanin coloration, (shoot about 20 cm. long); mature leaf color — top near 136A to 136B, underside near 137C.
(4) *Shape.*—Broad oval.
(5) *Texture.*—Upper side is flat to slightly gloss; underside is matte.
(6) *Edge.*—Serrate.
(7) *Serration.*—Serrulate, acuminate apices.
(8) *Leaf stem.*—color — near 138A.
(9) *Stipules.*—Long, simple, green color same as stem and light green center mid line.
(10) *Leaflets.*—Cross section — slight concave; weak to medium undulation of margin; terminal leaflet — long medium width; about 11 cm. long, about 6.5 cm. wide; wedge-shaped base.
D. Wood:
(1) *New wood.*—color — young shoots have weak anthocyanin; coloration — bronze
(2) *Old wood.*—Color — Near 138A.
E. Prickles (thorns):
(1) *Prickles.*—Present; quantity (main stalk) basal shoots have ordinary number of large prickles for the class and larger than ordinary number of small prickles; upper branches have ordinary number of large prickles and none to few small prickles. Position — irregular.

What is claimed is:

1. A new and distinct hybrid tea rose plant of the variety substantially as shown and described.

* * * * *

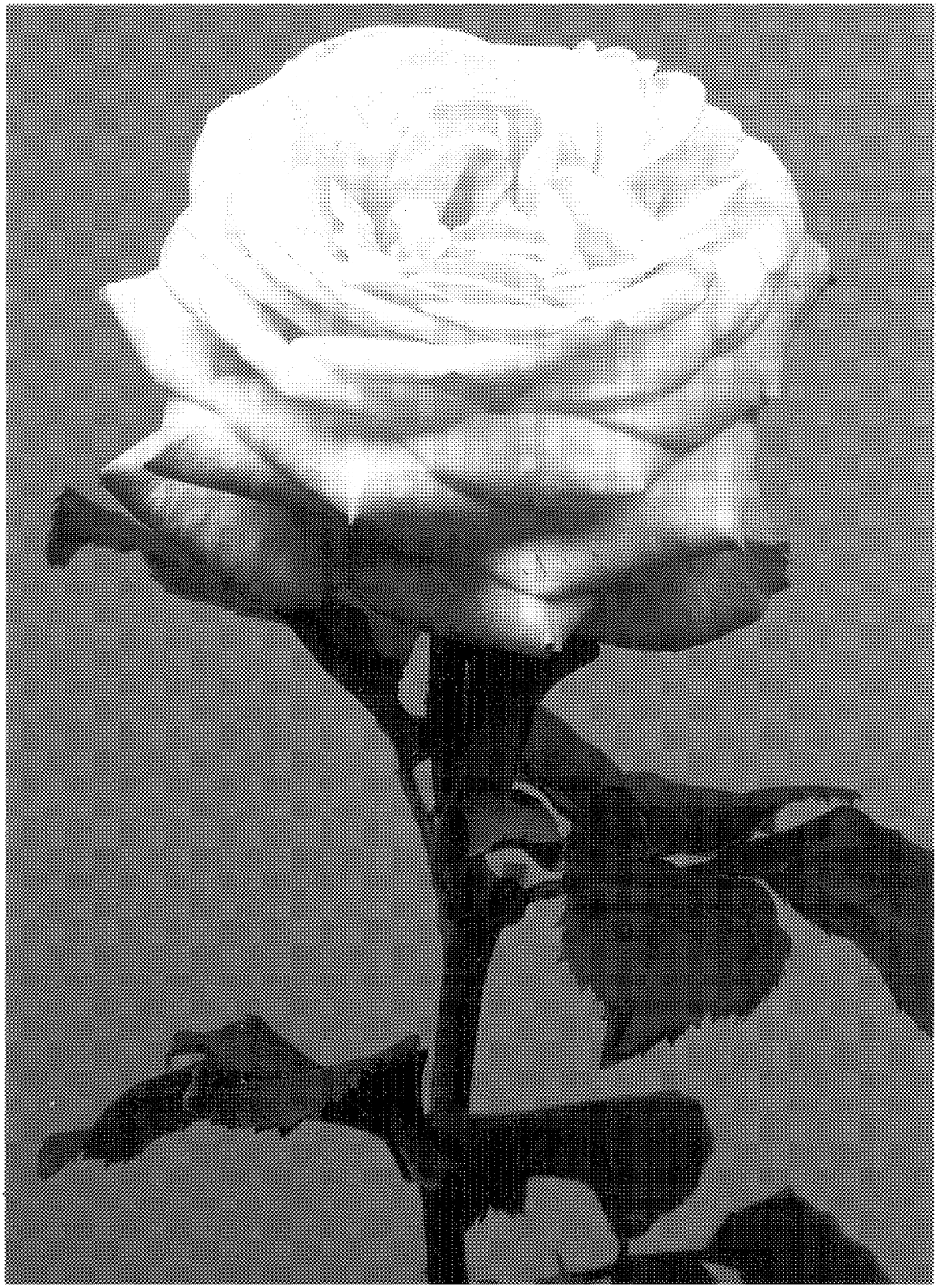

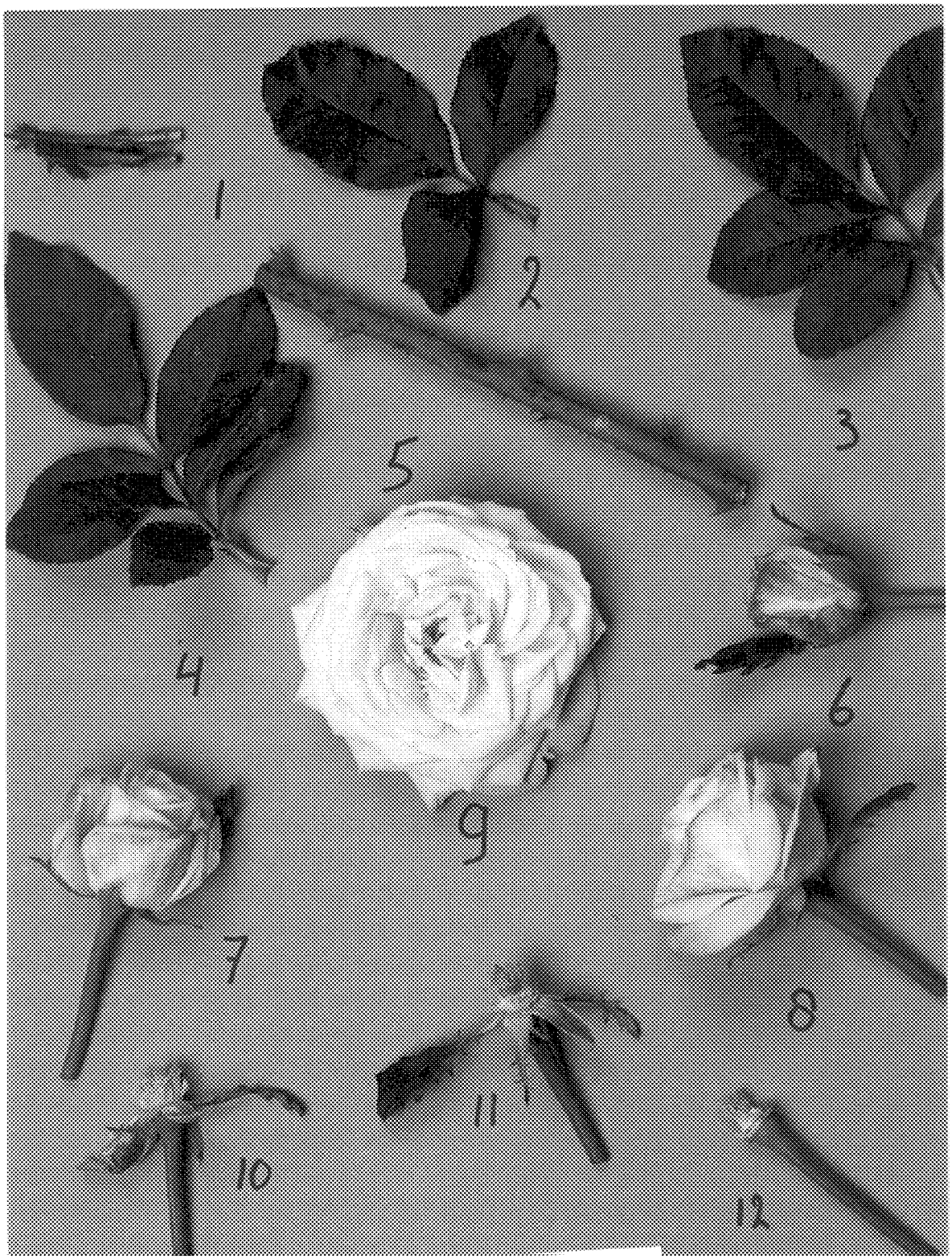
1
2
3
4
5
6
7
8
9
10
11
12